US008526706B2

(12) United States Patent
Verreet

(10) Patent No.: US 8,526,706 B2
(45) Date of Patent: Sep. 3, 2013

(54) METHOD AND DEVICE FOR INSPECTING A TRAVELING WIRE CABLE

(75) Inventor: Roland Verreet, Aachen (DE)

(73) Assignee: Casar Drahtseilwerk Saar GmbH, Kirkel (DE)

(*) Notice: Subject to any disclaimer, the term of this patent is extended or adjusted under 35 U.S.C. 154(b) by 0 days.

(21) Appl. No.: 13/559,286

(22) Filed: Jul. 26, 2012

(65) Prior Publication Data

US 2012/0294506 A1 Nov. 22, 2012

Related U.S. Application Data

(62) Division of application No. 12/083,415, filed as application No. PCT/EP2006/009908 on Oct. 13, 2006, now Pat. No. 8,254,660.

(30) Foreign Application Priority Data

Oct. 20, 2005 (DE) .................. 10 2005 050 220

(51) Int. Cl.
*G06K 9/00* (2006.01)
(52) U.S. Cl.
USPC ........................................... 382/141
(58) Field of Classification Search
USPC ........................ 382/141; 356/430
See application file for complete search history.

(56) References Cited

U.S. PATENT DOCUMENTS

| 3,074,631 A | * | 1/1963 | Buysch .................. 377/6 |
| 3,334,238 A | * | 8/1967 | Heimbold ............ 250/559.45 |
| 3,599,223 A | | 8/1971 | Bridebaugh et al. |
| 3,718,976 A | | 3/1973 | Nippert |
| 3,761,177 A | | 9/1973 | Corse |
| 4,099,244 A | * | 7/1978 | Galanis et al. ........ 382/141 |
| 4,877,323 A | * | 10/1989 | Stillwagon ............ 356/23 |
| 4,887,155 A | | 12/1989 | Massen |

FOREIGN PATENT DOCUMENTS

| DE | 19742177 | 4/1999 |
| EP | 0271728 | 6/1988 |
| EP | 0565906 | 10/1993 |

* cited by examiner

*Primary Examiner* — Tarifur Chowdhury
*Assistant Examiner* — Jonathon Cook
(74) *Attorney, Agent, or Firm* — Lucas & Mercanti, LLP; Klaus P. Stoffel

(57) ABSTRACT

A wire cable is exposed to flashes and the exposed image is detected on at least one lay length or a multiple of the lay length and monitored for changes in the image. Preferably, the respective repetition of the same outer stranded wire of the traveling wire cable is detected in the same location and every repetition or every other repetition or every third repetition is used for triggering the flash. In another embodiment, a picture is taken of a large portion of the wire cable using a specialized camera and the image is split up, into recurring units of length that correspond to the size of a lay length or a multiple of the lay length and the successive units of length are compared and inspected for changes in the image.

3 Claims, 3 Drawing Sheets

2 cm

METHOD AND DEVICE FOR INSPECTING A TRAVELING WIRE CABLE

CROSS-REFERENCE TO RELATED APPLICATIONS

The present application is a Divisional Application of U.S. patent application Ser. No. 12/083,415, filed Apr. 11, 2008, which is a 371 of International application PCT/EP2006/009908, filed Oct. 11, 2006, which claims priority of DE 10 2005 050 220.2, filed Oct. 20, 2005, the priority of these applications is hereby claimed and these applications are incorporated herein by reference.

BACKGROUND OF THE INVENTION

The invention relates to a method for inspecting a traveling wire cable.

It further relates to a device for carrying out the method.

Wire cables per se are to be examined visually on a daily basis for wire breaks and the occurrence of other faults. This cannot be carried out in practice. In order to be examined, the wire cable must be stationary or travel very slowly, and the work must be interrupted.

Magnetoinductive wire cable testing on traveling cables is possible, but complicated.

SUMMARY OF THE INVENTION

It is the object of the invention to make available a further, simple method for inspecting a traveling wire 25 cable.

In accordance with the invention, it is provided in a first version that the traveling wire cable is photographed at a stationary position at time intervals that are equal to the quotient of the lay length or a multiple of the lay length, and the travel speed of the wire cable, at least on one lay length or said multiple of the lay length, and the successive pictures are compared at least on one lay length or said multiple of the lay length, and are monitored for changes in the image that indicate damage.

In a second version, it is provided that the traveling wire cable is illuminated with light flashes at a stationary position at time intervals that are equal to the quotient of the lay length, or a multiple of the lay length, and the travel speed of the wire cable, at least on a lay length or said multiple of the lay length, and the illuminated image is detected at least on a lay length or said multiple of the lay length, and is monitored for changes in the image that indicate damage.

The twisted strands of a wire cable appear again after one lay length at the same position of the cable circumference. Successive sections of the wire cable of the size of the lay length therefore exhibit the same strand picture, each strand lies again at the same position. This then likewise holds for sections whose size is a multiple of the lay length.

The wire picture within the strands is displaced in this case, as a rule. It remains exactly the same, that is to say each wire lies again at the same position, only when the lay length of the wires in the strand are at a specific ratio to the lay length of the strands in the cable. It remains apparently the same when the wires are displaced by exactly one wire thickness or an integral multiple of the wire thickness.

If a traveling wire cable is always photographed or flashed by a camera arranged in a stationary fashion, or a stroboscope arranged in a stationary fashion whenever exactly one lay length or a multiple of the lay length has traveled past, the image photographed, or the image rendered visible against a sufficiently darker background by the light flashes is always the same. Starting from a specific frequency (image frequency approximately 24 per second), the images merge in front of the eye to form an uninterrupted image.

A "still image" of the strands is produced. The wires within the strands "migrate" slowly as a rule, and the strands seem to rotate about their own axis.

Damage in the wire cable causes a variation that is very quickly over, mostly cannot be detected pictorially, but is perceptible, or a visible change in the migratory movement of the wires.

The eye does not become tired when viewing the invariable or slowly migrating image. If a variation is perceived, the fault thereby discovered is examined in more detail later.

The variant of the flash illuminations is provided chiefly for immediate, direct viewing with the eye. The variant of photographing likewise later permits viewing with the eye. However, it can also be automized in a fashion ranging from partially to completely.

According to an advantageous refinement of the invention, the respective return of the same outer strand of the traveling wire cable at the same position is detected, and each, or each second or third, return is used to trigger shooting or the light flash. Consequently, the correct instant for the next picture or flash illumination is respectively ensured in a simple way, even when there is a change in the time intervals when starting up or braking the wire cable, or for other reasons such as certain changes in lay length over the length of a hanging cable.

However, there are also other possibilities in principle. For example, the travel speed of the wire cable can be picked off at the drive of the drive pulley of the cable, and said quotient can be constantly recalculated by a computer and the time sequence of the shootings or light flashes can be correspondingly controlled. If there is also a change in the lay length, this can be acquired with the aid of a separate lay length transmitter and also be input for the purpose of calculating the quotient.

The return of the strand is expediently acquired by detecting all the strands, preferably by means of a proximity sensor responding to the strand bulge, and by counting the strands. That is to say, in the case, for example, of six strands in the outer ply each sixth strand bulge belongs to the same ply and triggers the shooting or the light flash. If the cable feed is simultaneously measured between the return of the same strand, this information can be used to establish a possible variation in lay length as a function of the cable length. It can be advantageous in this case to acquire the return of the same strand with the aid of a number of sensors arranged in an offset fashion. It can be established in this way whether, for example, the intervals between two successive perceptions of the same strand have been shortened by an actual shortening of the cable lay length or by a twisting of the cable between the sensor positions.

According to a further refinement of the invention, the return of the strand is acquired by detecting a marking of the strand.

By way of example, the marking can be optical, for example it can consist of copper plating or of a magnetization, or can be a radioactive marking. To this extent, the invention also covers the production of wire cables that are prepared from the start to be inspected later.

This also holds for the further proposal of respectively marking a wire of the outer strands in a visible fashion, in order to render the migration of the wires in the strands visible in a more effective fashion.

According to a further refinement of the invention, the detection of the return of the same strand of the traveling wire cable is, furthermore, used, by recording the return of the strand or recording the bulge, to track the position of the wire cable that is respectively located at said stationary position, and to record the location of damaged positions on the wire cable starting therefrom.

This would also be possible, however, by means of a separate position pickup.

The damaged positions can then be examined more accurately later.

The length of the wire cable detected in the image need not be limited to a lay length or said multiple of the lay length. If it is larger, a fault can simply appear twice in the image. This need not, however, result in irritation, but can even lead to enhancing the perception.

An advantageous refinement of the mode of procedure consists in that on the basis of a change perceived in the acquired image the relevant damaged position is photographed with a high resolution camera at a position lying downstream of said stationary position in the travel direction of the wire cable.

When making a direct visual examination, it is possible if appropriate also immediately to run the wire cable backward and search for and examine the damaged position.

As a rule, the method is carried out simultaneously from various sides in order to detect the entire cable circumference.

A device for carrying out the method has in a station traversed by the wire cable a camera that is directed onto the wire cable and is connected to a controller; an evaluation and recording device is connected to the camera.

As a rule, the camera or photocell is multiply present and is directed onto the wire cable from various sides in order to detect the circumference of the wire cable completely.

The controller and the evaluation and recording device are preferably common to the various cameras or photocells.

Finally, in a third version of the invention it is provided that the traveling wire cable is photographed on a large length and the picture is decomposed into recurring length units for example of the size of a lay length or a multiple of the lay length, and the successive length units are compared and examined for changes in the image that indicate damage.

The decomposition, aimed at the possibility of shooting the entire wire cable, into the length units can be undertaken by a manual method or, preferably, automatically with the aid of a computer. The length units can then be further processed in the same way as if they had, as described above, resulted directly as a sequence of images from repeated triggering of the camera.

In order to produce an image, preferably a digital one, in the width of the cable diameter and in the length of the entire cable, it is possible, for example, to apply the same technique of exposure by a slit-shaped diaphragm as is used when taking analog or digital panorama photos. All that remains is to swing the camera or the lens; the image section imaged by the slit is varied by the travel of the wire cable itself. It is necessary only to synchronize the speed of the camera with the cable speed.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

BRIEF DESCRIPTION OF THE DRAWING

The aim below is to explain the invention further with the aid of drawings, in which.

DETAILED DESCRIPTION OF THE INVENTION

Figures 1, 2:
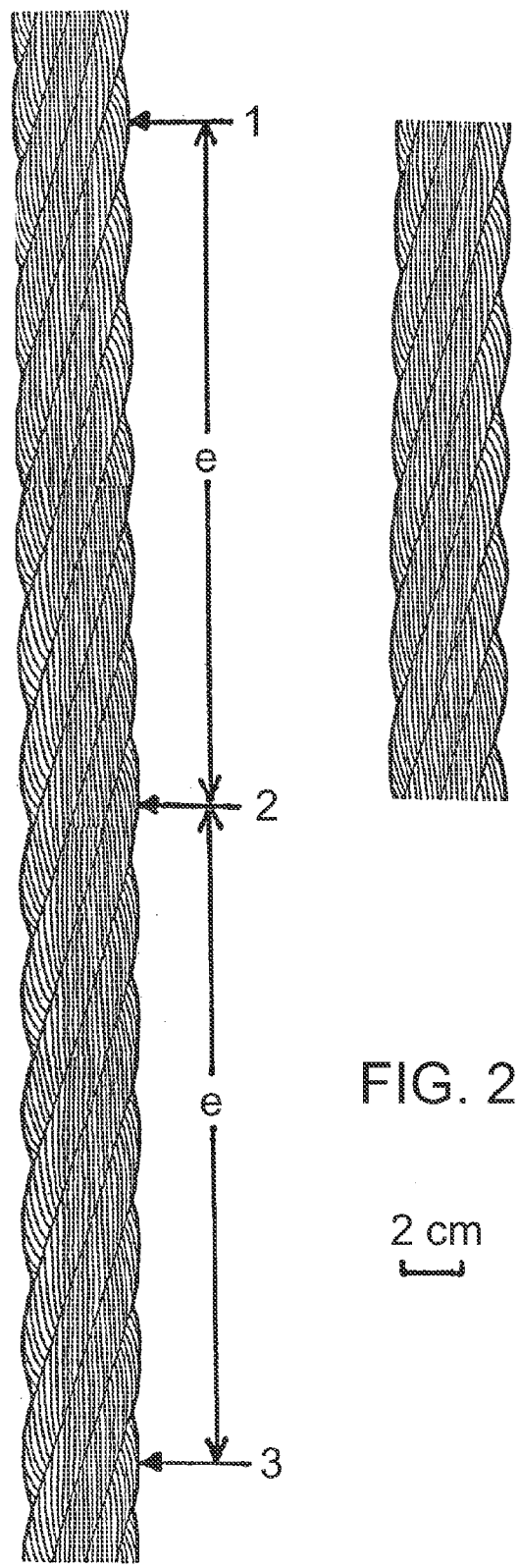
FIG. 1 shows a section of a wire cable.
FIG. 2 shows a section of FIG. 1.

In FIG. 1, the arrows 1, 2 and 3 point to the successive occurrence of the same strand at the same position, offset in each case by the lay length e, of the cable circumference of a wire cable 10.

The same strands in the same configuration are visible between the arrows 1 and 2 and between the arrows 2 and 3.

Figures 3, 4, 5:
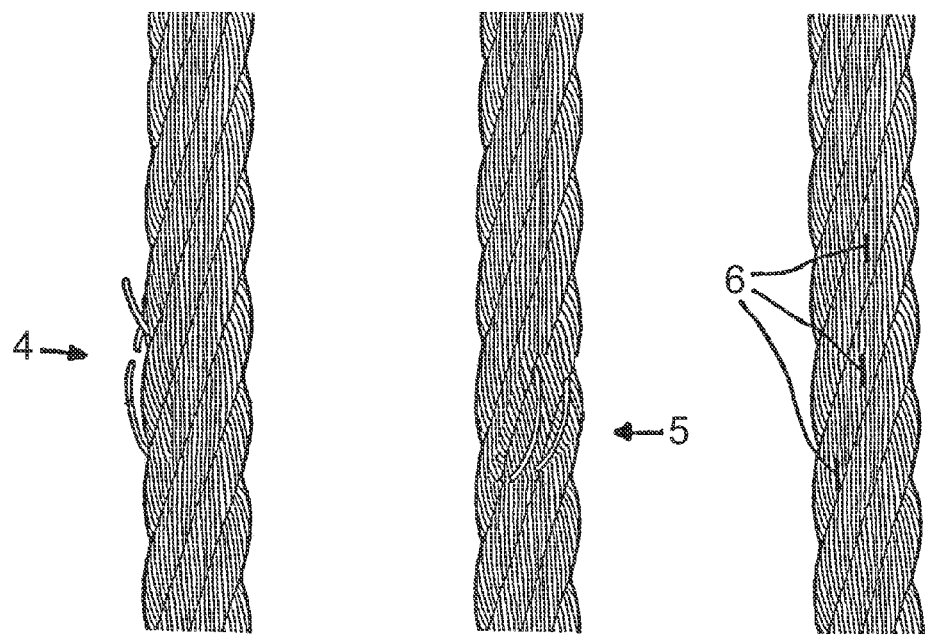
FIG. 3 shows a second section, corresponding to FIG. 2.
FIG. 4 shows a third section, corresponding to FIG. 2.
FIG. 5 shows a fourth section, corresponding to FIG. 2.

This configuration is illustrated per se in FIG. 2. It is respectively illustrated once again in FIGS. 3, 4 and 5, there with wire breaks 4 and 5 and 6, respectively. The wire breaks 4 and 5 are illustrated exaggeratedly. At the wire breaks 6, the wire has merely retracted somewhat and left a gap that has filled with dirt and lubricant and is to be recognized as a short dark line.

Figure 6:
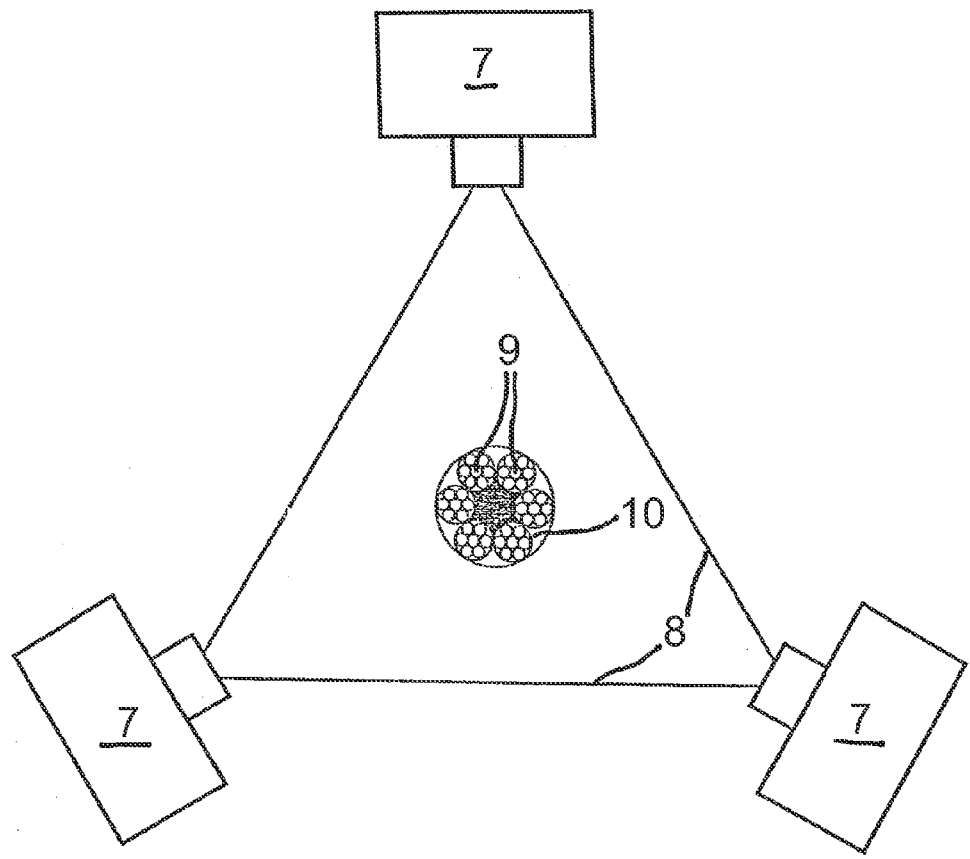
FIG. 6 shows, schematically as an exemplary embodiment, a device for inspecting a traveling wire cable.

FIG. 6 shows a station with three camera 7 directed onto the wire cable 10 from various sides. Lines 8 mark the regions acquired by the cameras 7.

The lay length of the strands 9 of the wire cable 10 is 250 mm in the present example, the travel speed of the wire cable 10 perpendicular to the plane of the drawing is 5 m/sec, and the flash frequency of the camera is 20 hertz. That is to say, the wire cable is photographed at intervals of 0.05 sec whenever the next section of the wire cable of the size of the lay length is located in front of the cameras 7.

For the rest, reference may be made to the explanations given further above.

While specific embodiments of the invention have been shown and described in detail to illustrate the inventive principles, it will be understood that the invention may be embodied otherwise without departing from such principles.

I claim:

1. A method for inspecting a traveling wire cable, comprising the steps of:
    illuminating the traveling wire cable with light flashes at a stationary position at time intervals that are equal to the quotient of a lay length, or a multiple of the lay length, and the travel speed of the wire cable, at least on one lay length or said multiple of the lay length, wherein the light flashes illuminate the wire cable so that twisted strands of the wire cable subsequently appear in an image in the same position of the cable circumference and structure of the wire cable is visible in the image; and
    detecting the illuminated image at least on the lay length or said multiple of the lay length, and is monitoring for changes in the image that indicate damage.

2. A method for inspecting a traveling wire cable, comprising the steps of:
    photographing the traveling wire cable on a large length;
    decomposing a picture into recurring length units of the size of a lay length or a multiple of the lay length; and
    comparing the successive length units and examining for changes in the wire cable that indicate damage.

3. The method as claimed in claim 2, wherein the traveling wire cable is photographed by means of a camera in which continuous shooting synchronized with the travel speed of the wire cable is produced by applying a slit diaphragm.

* * * * *